United States Patent [19]

Bartholomaeus

[11] Patent Number: 5,601,842
[45] Date of Patent: Feb. 11, 1997

[54] SUSTAINED RELEASE DRUG FORMULATION CONTAINING A TRAMADOL SALT

[75] Inventor: Johannes H. A. Bartholomaeus, Aachen, Germany

[73] Assignee: Gruenenthal GmbH, Aachen, Germany

[21] Appl. No.: 585,741

[22] Filed: Jan. 16, 1996

Related U.S. Application Data

[63] Continuation of Ser. No. 300,325, Sep. 2, 1994, abandoned.

[30] Foreign Application Priority Data

Sep. 3, 1993 [DE] Germany .................. 43 29 794.3

[51] Int. Cl.$^6$ ........................ A61K 9/22; A61K 9/28
[52] U.S. Cl. ............. 424/464; 424/469; 424/474; 424/480; 424/482; 424/488
[58] Field of Search ................. 424/488, 469, 424/474, 480, 482

[56] References Cited

U.S. PATENT DOCUMENTS

| | | | |
|---|---|---|---|
| 4,389,393 | 6/1983 | Schor et al. | 424/468 |
| 4,968,508 | 11/1990 | Oren et al. | 424/469 |
| 5,073,379 | 12/1991 | Klimesche et al. | |
| 5,126,145 | 6/1992 | Evenstad et al. | 424/468 |
| 5,132,116 | 7/1992 | Sournac et al. | 424/469 |
| 5,268,181 | 12/1993 | O'Neill et al. | 424/468 |

FOREIGN PATENT DOCUMENTS 147780  7/1985  European Pat. Off. .

OTHER PUBLICATIONS

Dow Chemical Brochure "Formulating for Controlled Release with METHOCEL Premium Cellulose Ethers" (1987).
Lapidus et al., "Drug Release from . . . ", *J. Pharmaceutical Sci.*, vol. 57, No. 8, pp. 1292–1301 (1968).
Alderman, "A Review Of . . . ", *Int. J. Pharm. Tech. & Prod. Mfr.*, vol. 5, No. 3, pp. 1–9 (1984).
Ford et al., "Importance of drug", *Int. J. Pharmaceutics*, vol. 40, pp. 223–234 (1987).

*Primary Examiner*—Amy Hulina
*Attorney, Agent, or Firm*—Evenson, McKeown, Edwards & Lenahan, P.L.L.C.

[57] ABSTRACT

A drug formulation of tramadol or a tramadol salt in orally administrable tablet form containing at least one pharmaceutically acceptable matrixing agent is disclosed from which a non-moisture sensitive, physiologically acceptable tramadol salt is sustained released.

9 Claims, 3 Drawing Sheets

SUSTAINED RELEASE DRUG FORMULATION CONTAINING A TRAMADOL SALT

This application is a continuation of application Ser. No. 08/300,325 now abandoned, filed Sep. 2, 1994.

BACKGROUND OF THE INVENTION

This invention relates to drug formulations in form of tablets for oral administration from which a non-moisture sensitive, physiologically acceptable salt of tramadol is released in a sustained manner and which contain at least one pharmaceutically acceptable matrixing agent.

Tramadolhydrochloride-(1RS;2RS)-2-[(dimethylamino)methyl]-1-(3-methoxyphenyl)cyclohexanol, hydrochloride—is an analgesic effective in severe and moderate severe pain. All drug formulations available on the market are immediate release forms which require administration 3 to 4 times per day in order to achieve good therapeutic effectiveness in relieving chronic pain. It would be a desirable relief to the patients if the frequency of administration could be reduced to once or twice daily.

Several principles of sustained release formulations are known to a person skilled in the art. For example, U.S. Pat. No. 3,065,143, filed on Apr. 19, 1960, discloses a sustained release tablet containing at least one-third part by weight of the weight of the tablet of a pharmaceutically acceptable hydrophilic gum which rapidly absorbs water and swells at 37° C. to form a soft mucilaginous gel barrier on the surface of the tablet when brought into contact with the aqueous fluids of the gastrointestinal tract which prevents rapid disintegration of the tablet and release of the medicament contained therein when taken orally, but allows slow disintegration of the tablet and release of medicament over a period of at least four hours. However, the examples show that the release of the medicament is influenced by the pH value. For the release mechanism it is further described that the soft mucilaginous gum gel barrier is worn away by the motion of the tablet in the gastrointestinal tract, and some of the admixed medicinal agent is carried away with it and released. At the same time the protective coating at the surface of the tablet is renewed. This means that the release of the medicament is also influenced by mechanical stress. Further it is described that the rate of release depends on the weight ratio of active ingredient to gum as well as on the content of hydrophilic gum in the tablet.

In U.S. Pat. No. 4,389,393 (Reexamination Certificate B1 4,389,393) a carrier base material for moisture sensitive active ingredients is disclosed which is shaped and compressed to a solid unit dosage form and has a regular and prolonged release pattern upon administration. The carrier base material consists of one or more hydroxypropylmethylcelluloses or a mixture of one or more hydroxypropylmethylcelluloses and up to 30% by weight of the mixture of methylcellulose, sodium carboxymethylcellulose and/or other cellulose ether, wherein at least one of the hydroxypropylmethylcelluloses has a methoxy content of 16–24% by weight, a hydroxypropyl content of 4–32% by weight and a number average molecular weight of at least 50,000. The carrier base material constitutes 30% by weight or less of the solid unit dosage form and causes that at least four hours are required for the release of 94.4% of the moisture sensitive active ingredient from the dosage form following administration.

In *Int. J. Pharm. Tech. & Prod. Mfr.* 5, 1 (1984) hydrophilic matrices, especially hydroxypropylmethylcelluloses, are described for oral dosage forms with controlled release. On pages 4 to 6 it is explained that the rate of drug release depends on the viscosity as well as on the amount of the employed polymer. Furthermore size and shape of the dosage unit influence the release, whereas practically no dependence on the manufacturing process by granulation or by direct tabletting is observed. On the other hand different fillers show a pronounced influence on the drug release. According to FIGS. 16 and 18, insoluble excipients cause an acceleration of the release up to complete suppression of the controlled release effect, independent of whether these compounds are swellable such as microcrystalline cellulose or are not swellable such as calcium hydrogen phosphate.

From *Int. J. Pharm.* 40, 223 (1987) it is known that the rate of drug release from a sustained release tablet containing hydroxypropylmethylcellulose as the matrixing agent depends on the weight ratio of active substance to hydroxypropylmethylcellulose. The more this ratio is shifted in favor of the active substance, the higher the rate of release. In formulations having a filler content which is more than 50% by weight, the rate of release is influenced by the types of adjuvants employed. A partial replacement of hydroxypropylmethylcellulose with a filler and a consequent reduction of the hydroxypropylmethylcellulose content in the dosage form leads to an increase in the release rate.

The matrix sustained release tablets described in *J. Pharm. Sci.* 57, 1292 (1968) lead to an increased release rate when increasing the soluble portions in the hydrophilic matrix.

SUMMARY OF THE INVENTION

It is the object of the present invention to provide a drug in tablet form for oral administration from which a non-moisture sensitive, well tolerated salt of tramadol is released in a prolonged manner independent on the pH value of the release environment and on the type and amount of the fillers.

A further object is to provide a sustained release formulation of tramadol which should be independent of the active ingredient content and of the amount of the matrixing agent for a given mass and shape of the tablet.

These and other objects of the invention are achieved by providing a drug formulation in tablet form with sustained release of the active ingredient containing at least one non-moisture sensitive, physiologically acceptable salt of tramadol as active ingredient and at least one cellulose ether and/or cellulose ester which has a viscosity between 3,000 and 150,000 mPas in a 2% by weight aqueous solution at 20° C. as pharmaceutically acceptable matrixing agent.

As used herein, the term "Release profile" refers to the amount of active ingredient released in % by weight of the total content of active ingredient plotted versus the duration of the test.

DETAILED DESCRIPTION OF PREFERRED EMBODIMENTS

Figure 1:
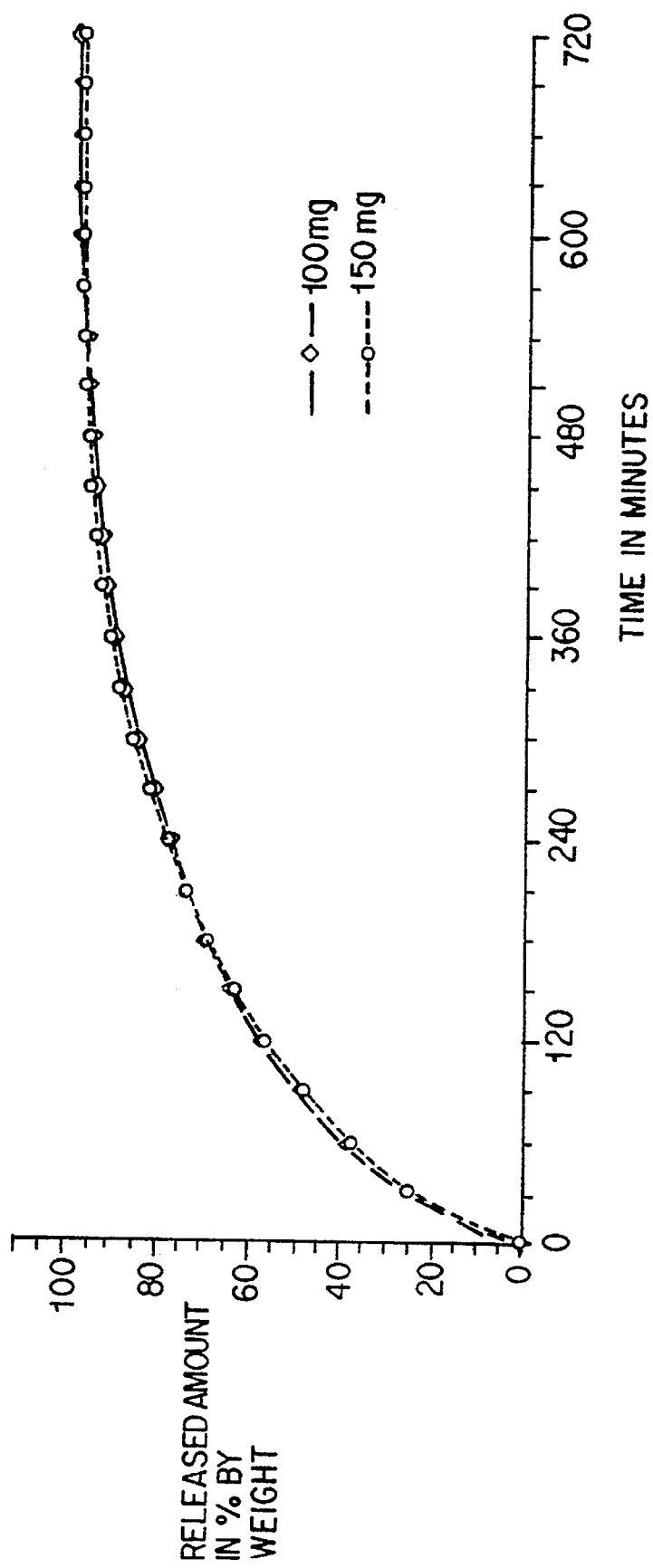
FIG. 1 is a graph of the in vitro release curve of tramadol hydrochloride from tablets prepared according to Example 1.

It has been found that the high requirements put on a tramadol salt containing sustained release formulation are fulfilled by a tablet formulation containing a non-moisture sensitive salt of tramadol and a selected pharmaceutically acceptable matrixing agent.

The invention accordingly relates drug formulations in tablet form with sustained release of the active ingredient containing at least one non-moisture sensitive, physiologically acceptable salt of tramadol as active ingredient and at least one cellulose ether and/or cellulose ester which comprises a viscosity between 3,000 and 150,000 mPas in a 2% by weight aqueous solution at 20° C. as pharmaceutically acceptable matrixing agent.

Cellulose ethers and/or cellulose esters having a viscosity between 10,000 and 150,000 mPas in a 2% by weight aqueous solution at 20° C. are preferred as pharmaceutically acceptable matrixing agents. Particularly suitable pharmaceutically acceptable matrixing agents are selected from the group consisting of methylhydroxypropylcelluloses, hydroxyethylcelluloses, hydroxypropylcelluloses, methylcelluloses, ethylcelluloses, and carboxymethylcelluloses and most particularly selected from the group consisting of methylhydroxypropylcelluloses, hydroxyethylcelluloses, and hydroxypropylcelluloses.

In drug formulations according to the invention the content of active ingredient to be released in a prolonged manner is in the range of 10 to 85% by weight and the content of pharmaceutically acceptable matrixing agent is in the range of 10 and 40% by weight. Drug formulations with an active ingredient content to be released in a prolonged way in the range of 25 to 70% by weight and a pharmaceutically acceptable matrixing agent content in the range of 10 to 40% by weight are especially preferred.

The tablets according to the invention may contain conventional pharmaceutical excipients such as fillers, e.g. lactose, microcrystalline cellulose or calcium hydrogen phosphate, as well as, lubricants and glidants, e.g. colloidal silicon dioxide, talc, magnesium stearate and/or stearic acid, in an amount between 0 and 80% by weight, preferably between 5 and 65% by weight.

In many cases the rate of release of an active ingredient from a drug formulation depends on the pH value. During the gastrointestinal passage of the drug formulation, the pH value may vary from less than 1 to about 8. These fluctuations may vary from one recipient of the drug to another. There can also be variations in the pH value-versus-time-profile during the gastrointestinal passage in the same person from one administration to another. A dependency on the pH value of the release rate of the active ingredient can lead in vivo to different release rates. The release profiles of a tramadol salt from a drug formulation according to the invention, however, are surprisingly independent of pH values which may occur during the gastrointestinal passage. The release profiles at surrounding pH values of 1.2, 4.0 and 6.8 are coincident to each other as well as to the release during a pH value-versus-time-profile starting from pH 1.2 through pH 2.3 and pH 6.8 up to pH 7.2.

In contrast to the mentioned prior art the release rate of a tramadol salt from a drug formulation according to the invention is independent of the viscosity of the matrixing agent in the range between 3,000 and 150,000 mPas for a 2% by weight aqueous solution as well as of the content of the matrixing agent and the filler. Furthermore, the release profile of a tramadol salt containing sustained release tablet according to the invention is not significantly affected by whether the filler used is a water soluble one such as lactose; an insoluble, non-water swellable filler such calcium hydrogen phosphate; or an insoluble, water swellable filler such as microcrystalline cellulose, provided the size and shape of the tablet and the composition with respect to the active ingredient, the matrixing agent and the optional components are kept constant. All these drug formulations show coinciding release profiles.

Because of the high water-solubility, particularly of tramadolhydrochloride, and with regard to the teaching of the prior art that the content of soluble compounds in a drug formulation has an-influence on the release rate, it was expected that formulations with different contents of a tramadol salt would have different release profiles. Further it was expected that a change in the ratio of tramadol salt to matrixing agent also would lead to a change in the release profile. Surprisingly, it has been found that drug formulations according to the invention with different contents of active ingredient in which the overall content of the non-moisture sensitive, physiologically acceptable tramadol salt and the soluble or insoluble filler is kept constant, show coinciding release profiles provided the tablet's size, shape, total mass and composition regarding the matrixing agent and the optional excipients remain unchanged.

Drug formulations according to the invention may be simple tablets as well as coated tablets such as film-coated or sugar-coated tablets. One or more coating layers can be applied to the coated tablets. Suitable coating materials include e.g. the well known methylhydroxypropylcelluloses which affect the release profile only to a minor extent. Known diffusion coatings e.g. composed of swellable, but water-insoluble poly(meth)acrylates lead to an even more retarded release from drug formulations according to the invention. The slow releasing tablet core, which has an active ingredient content preferably between 10 and 85% by weight, most preferably between 25 and 70% by weight, may be coated with additional active ingredient, which is immediately released as an initial dose, by various known methods, e.g. by sugar-coating like methods, by spraying of solutions or suspensions, or by powder layering. Further suitable tablet forms include multi-layer and inlay type tablets. At least one tramadol salt is contained in a range of preferably 10 to 85% by weight, most preferably 25 to 70% by weight, in one or more layers of the multi-layer tablet or in the core of the inlay type tablet and is sustained released from this part of the tablet, whereas the release of a tramadol salt from one or more layers of the multi-layer tablet or from the outer shell of the inlay type tablets is unsustained. Multi-layer and inlay type tablets may also comprise one or more layers, shells or coatings without active ingredient.

The preparation of drug formulations according to the invention is characterized by a high reproducibility of the release properties of the resulting tramadol salt containing compositions. During a storage of at least one year there is no change in the release profile of drug formulations according to the invention.

Once or twice daily administration of a tablet according to the invention leads to good therapeutical effectiveness in patients with severe chronic pain.

EXAMPLE 1

Matrix tablets consisting per tablet of:

| | |
|---|---|
| Tramadolhydrochloride | 100 mg |
| Methylhydroxypropylcellulose type 2208, 100,000 mPas (Manufacturer: Dow Chemical Company, Midland, Mich.) | 85 mg |
| Calcium hydrogen phosphate | 62 mg |
| colloidal silicon dioxide | 5 mg |
| Magnesium stearate | 3 mg | were prepared in a batch size of 200 g by sieving all components through a 0.63 mm sieve, mixing in a cube blender for 10 minutes and pressing into tablets having a diameter of 9 mm, a radius of curvature of 8.5 mm and a mean weight of 255 mg by means of a Korsch EK 0 eccentric press.

By using the same method matrix tablets consisting per tablet of:

| | |
|---|---|
| Tramadolhydrochloride | 150 mg |
| Methylhydroxypropylcellulose type 2208, 100,000 mPas | 85 mg |
| Calcium hydrogen phosphate | 12 mg |
| colloidal silicon dioxide | 5 mg |
| Magnesium stearate | 3 mg | were prepared.

The in vitro release of tramadolhydrochloride from the tablets was tested according to DAB 10 in a paddle apparatus. The temperature of the dissolution medium was 37° C., and the rotation speed of the paddle was 75 rpm. At the beginning of the test each tablet was placed in 600 ml of artificial gastric juice with a pH value of 1.2. After 30 minutes the pH value was raised to 2.3 by adding a sodium hydroxide solution, after further 90 minutes the pH value was raised to 6.5 and after another 60 minutes to 7.2. The amount of released active ingredient in the dissolution medium was measured by means of spectrophotometry. The following release values (mean of n=3) were determined:

| | Amount released in % by weight containing tramadolhydrochloride: | |
|---|---|---|
| Time in minutes | 100 mg | 150 mg |
| 30 | 26 | 25 |
| 60 | 39 | 37 |
| 120 | 57 | 56 |
| 300 | 84 | 86 |
| 720 | 99 | 98 |

The in vitro release curves of the tablets containing 100 mg or 150 mg of tramadolhydrochloride are given in FIG. 1.

EXAMPLE 2

Matrix tablets consisting per tablet of:

| | |
|---|---|
| Tramadolhydrochloride | 200 mg |
| Methylhydroxypropylcellulose type 2208, 100,000 mPas (Manufacturer: Shin Etsu, Tokyo, Japan) | 105 mg |
| Calcium hydrogen phosphate | 36 mg |
| colloidal silicon dioxide | 5 mg |
| Magnesium stearate | 4 mg | were prepared in a batch size of 525 g in the following manner: Tramadolhydrochloride, methylhydroxypropylcellulose, calcium hydrogen phosphate and 50% of the amount of silicon dioxide and magnesium stearate each were sieved through a 0.5 mm sieve and mixed in a cube blender for 10 minutes. The resulting mixture was pressed to briquettes with a diameter of 20 mm by means of a Korsch EK 0 press.

After breaking of the resulting briquettes by means of a 1 mm sieve, the remaining amounts of silicon dioxide and magnesium stearate were added and mixed followed by pressing the mixture into tablets of 10 mm diameter, 8 mm radius of curvature and a mean weight of 350 mg by means of a Korsch EK 0 press.

The in vitro release of the active ingredient was tested according to the procedure of Example 1. The following release values (mean of n=2) were obtained:

| | Amount released in % by weight |
|---|---|
| 30 | 22 |
| 60 | 32 |
| 120 | 48 |
| 300 | 76 |
| 720 | 100 |

EXAMPLE 3

The tablets prepared according to Example 2 were coated in with a lacquer by means of a Wurster process. The lacquer was composed of:

| | |
|---|---|
| Eudragit RL 30 D (Manufacturer: Rohm, Darmstadt, Germany) | 18.2% by weight |
| Talc | 8.2% by weight |
| Titanium dioxide | 6.5% by weight |
| Polyethylene glycol (Manufacturer: Hoechst AG, Frankfurt, Germany) | 1.6% by weight |
| Triethyl citrate | 1.1% by weight |
| Demineralized water | 64.4% by weight |

The coating caused an increase of the mean weight of the tablet cores by 20 mg. The in vitro release of the active ingredient from the film-coated tablets was tested according to the procedure given in Example 1. The following release values (mean of n=2) were obtained:

| Time in minutes | Amount released in % by weight |
|---|---|
| 30 | 10 |
| 60 | 22 |
| 120 | 39 |
| 300 | 69 |
| 720 | 96 |

EXAMPLE 4

As described in Example 2, tablets with a mean weight of 350 mg were prepared containing instead of calcium hydrogen phosphate 36 mg of microcrystalline cellulose PH 101 (manufacturer: FMC, Philadelphia, Pa.) and instead of methylhydroxypropylcellulose either 105 mg of methylhydroxypropylcellulose type 2208 with a viscosity of 15,000 mPas (manufacturer: Shin Etsu) or 105 mg of methylhydroxypropylcellulose type 2208 with a viscosity of 50,000 mPas (manufacturer: Shin Etsu). The in vitro release of the active ingredient was tested according to the procedure of Example 1. The following release values (mean of n=3) were obtained:

| Time in minutes | Amount released in % by weight from the tablet containing matrixing agent with a viscosity of: | |
| --- | --- | --- |
| | 15,000 mPas | 50,000 mPas |
| 30 | 23 | 23 |
| 60 | 35 | 34 |
| 120 | 51 | 50 |
| 300 | 79 | 79 |
| 720 | 103 | 103 |

Figure 2:
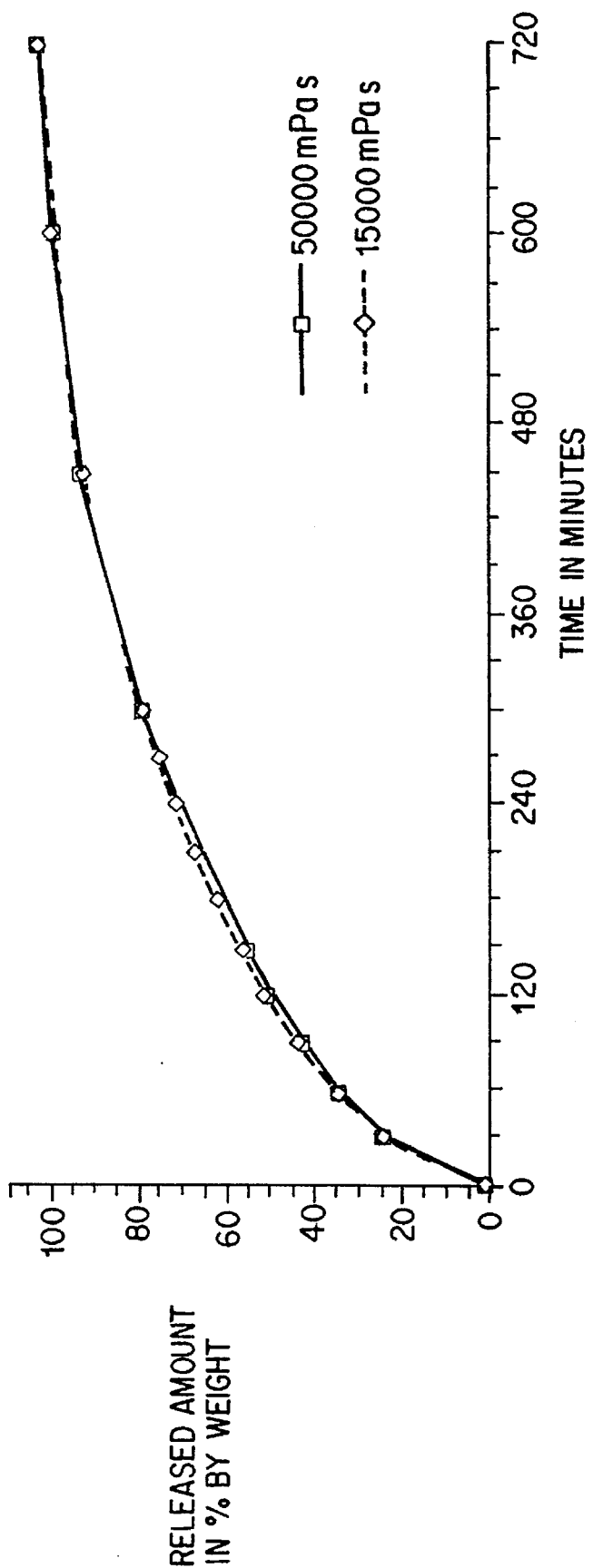
FIG. 2 is a graph of the in vitro release curve of tramadol hydrochloride from tablets prepared according Example 4.

The in-vitro release curves of the tablets containing methylhydroxypropylcellulose with a viscosity of 15,000 mPas and 50,000 mPas, respectively, are given in FIG. 2.

EXAMPLE 5

As described in Example 2, tablets with a mean weight of 350 mg and the following composition per tablet were prepared:

| | |
| --- | --- |
| Tramadolhydrochloride | 200 mg |
| Methylhydroxypropylcellulose type 2208, 50,000 mPas | 50 mg |
| (Manufacturer: Shin Etsu) | |
| microcrystalline cellulose PH 101 | 91 mg |
| colloidal silicon dioxide | 5 mg |
| Magnesium stearate | 4 mg |

The in vitro release of the active ingredient was tested according to the procedure of Example 1. The following release values (mean of n=3) were obtained:

| Time in minutes | Amount released in % by weight |
| --- | --- |
| 30 | 21 |
| 60 | 33 |
| 120 | 49 |
| 300 | 78 |
| 720 | 98 |

Figure 3:
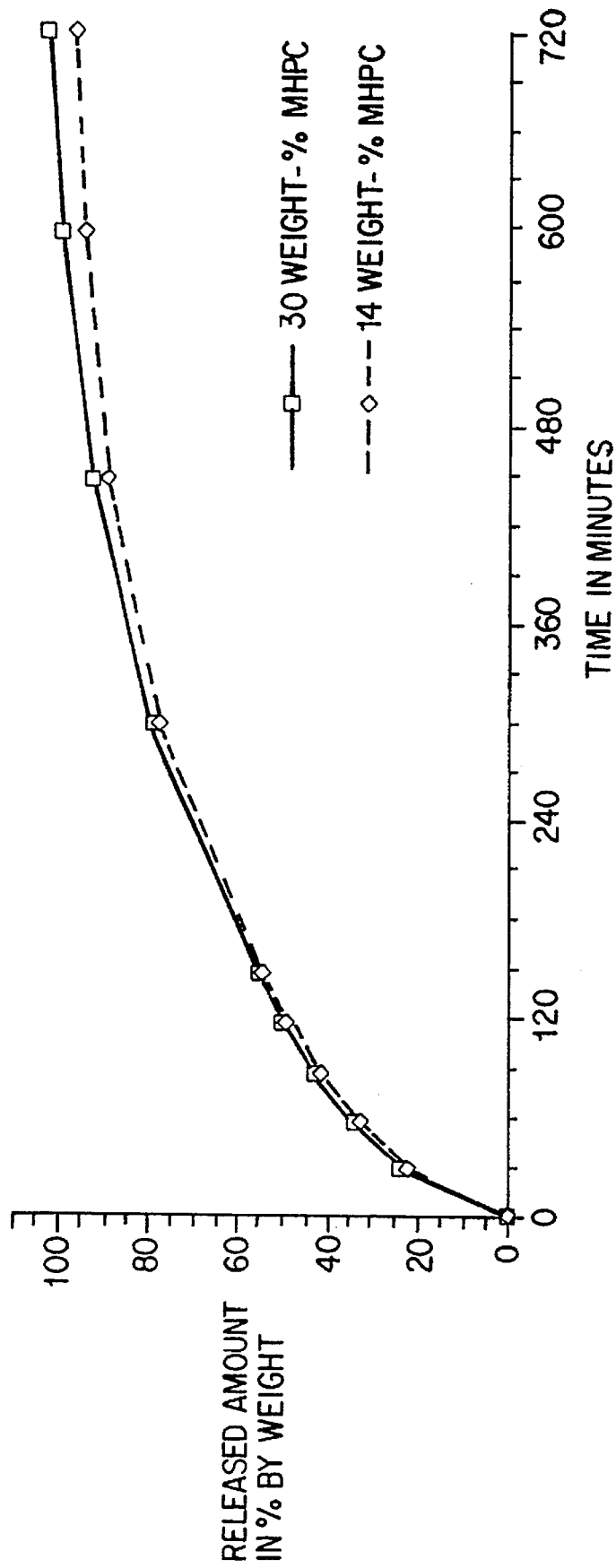
FIG. 3 is a graph of the in vitro release curve of tramadol hydrochloride from tablets prepared according to Examples 5 and 4.

The in vitro release curves of the tablets containing either 50 mg corresponding to 14% by weight or 105 mg corresponding to 30% by weight (see Example 4) of methylhydroxypropylcellulose with a viscosity of 50,000 mPas are given in FIG. 3.

EXAMPLE 6

Matrix tablets consisting per tablet of:

| | |
| --- | --- |
| Tramadolhydrochloride | 100 mg |
| Methylhydroxypropylcellulose type 2910, 10,000 mPas | 40 mg |
| (Manufacturer: Dow Chemical Company) | |
| microcrystalline cellulose PH 101 | 26 mg |
| colloidal silicon dioxide | 2 mg |
| Magnesium stearate | 2 mg | were prepared in a batch size of 510 g according to the procedure given in Example 2. The resulting tablets had a diameter of 8 mm, a radius of curvature of 7.5 mm and a mean weight of 170 mg.

The in vitro release of the active ingredient was tested according to the procedure of Example 1. The following release values (mean of n=2) were obtained:

| Time in minutes | Amount released in % by wieght |
| --- | --- |
| 30 | 25 |
| 60 | 40 |
| 120 | 59 |
| 300 | 89 |
| 720 | 105 |

EXAMPLE 7

Matrix tablets consisting per tablet of:

| | |
| --- | --- |
| Tramadolhydrochloride | 150 mg |
| Hydroxypropylcellulose, 30,000 mPas | 105 mg |
| (Klucel ™ HXF, Hercules, Duesseldorf, Germany) | |
| microcrystalline cellulose PH 101 | 86 mg |
| colloidal silicon dioxide | 5 mg |
| Magnesium stearate | 4 mg | were prepared in a batch size of 350 g according to the procedure given in Example 2. The in vitro release of the active ingredient was tested according to the procedure of Example 1. The following release values (mean of n=2) were obtained:

| Time in minutes | Amount released in % by weight |
| --- | --- |
| 30 | 25 |
| 60 | 35 |
| 120 | 50 |
| 300 | 75 |
| 720 | 100 |

EXAMPLE 8

Matrix tablets consisting per tablet of

| | |
| --- | --- |
| Tramadolhydrochloride | 150 mg |
| Hydroxyethylcellulose, 100,000 mPas | 105 mg |
| (Natrosol ™ HHX, Hercules, Duesseldorf, Germany) | |
| microcrystalline cellulose PH 101 | 86 mg |
| colloidal silicon dioxide | 5 mg |
| Magnesium stearate | 4 mg | were prepared in a batch size of 350 g according to the procedure given in Example 2. The in vitro release of the active ingredient was tested according to the procedure of Example 1. The following release values (mean of n=2) were obtained:

| Time in minutes | Amount released in % by weight |
| --- | --- |
| 30 | 20 |
| 60 | 32 |
| 120 | 48 |
| 300 | 75 |
| 720 | 100 |

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A drug formulation in tablet form with sustained release of an active ingredient, said drug formulation consisting essentially of from 10 to 85% by weight of non-moisture sensitive, physiologically acceptable tramadol hydrochloride as said active ingredient; from 10 to 40% by weight of at least one pharmaceutically acceptable matrixing agent selected from the group consisting of methylhydroxypropylcelluloses, hydroxyethylcelluloses and hydroxypropylcelluloses having a viscosity between 3,000 and 150,000 mPas in a 2% by weight aqueous solution at 20° C., and from 0 to 80% by weight of conventional excipients selected from the group consisting of fillers, lubricants, and glidants.

2. A drug formulation according to claim 1, wherein said matrixing agent has a viscosity between 10,000 and 150,000 mPas in a 2% by weight aqueous solution at 20° C.

3. A drug formulation according to claim 1, comprising from 25 to 70% by weight of said physiologically acceptable salt of tramadol and from 10 to 40% by weight of said pharmaceutically acceptable matrixing agent.

4. A drug formulation according to claim 1, which contains from 5 to 65% by weight of conventional excipients selected from the group consisting of fillers, lubricants, and glidants.

5. A drug formulation according to claim 1, further comprising a film coating.

6. A drug formulation according to claim 5, wherein said film coating comprises methylhydroxypropylcellulose.

7. A drug formulation according to claim 5, wherein said film coating comprises swellable, water-insoluble poly(meth)acrylate.

8. A drug formulation according to claim 5, wherein said film coating contains polyethylene glycol, talc and titanium dioxide.

9. A drug formulation in tablet form with sustained release of an active ingredient, said drug formulation consisting of from 10 to 85% by weight of non-moisture sensitive, physiologically acceptable tramadol hydrochloride as said active ingredient; from 10 to 40% by weight of at least one pharmaceutically acceptable matrixing agent selected from the group consisting of methylhydroxypropylcelluloses, hydroxyethylcelluloses and hydroxypropylcelluloses having a viscosity between 3,000 and 150,000 mPas in a 2% by weight aqueous solution at 20° C., and from 0 to 80% by weight of conventional excipients selected from the group consisting of fillers, lubricants, and glidants.

* * * * *